United States Patent [19]

Rubin

[11] 4,351,823

[45] Sep. 28, 1982

[54] DIAGNOSIS OF TUMORS OR BACTERIAL INFECTIONS HAVING β-GLUCURONIDASE ACTIVITY

[75] Inventor: David Rubin, c/o Israel Medical Foundation, P.O. Box 3592, Jerusalem, Israel

[73] Assignees: Adolf W. Schwimmer, Savyon; Irwin S. Schwartz, Tel Aviv; David Rubin, Jerusalem, all of Ill.X

[21] Appl. No.: 172,448

[22] Filed: Jul. 18, 1980

Related U.S. Application Data

[63] Continuation-in-part of Ser. No. 89,888, Oct. 31, 1979, Pat. No. 4,337,760, which is a continuation-in-part of Ser. No. 11,619, Feb. 12, 1979, Pat. No. 4,327,074, and a continuation-in-part of Ser. No. 951,270, Oct. 13, 1978, and a continuation-in-part of Ser. No. 951,269, Oct. 13, 1978.

[51] Int. Cl.$^3$ .................... A61K 49/00; C12Q 1/04; C12Q 1/44; G01N 33/50
[52] U.S. Cl. .................... 424/9; 23/230 B; 128/1 R; 424/7; 424/94; 424/180; 435/4; 435/19; 435/34
[58] Field of Search .................... 424/7, 9, 94, 180; 435/4, 19, 34; 23/2320 B; 128/1 R

[56] References Cited

U.S. PATENT DOCUMENTS 4,327,074  4/1982  Rubin ........................... 424/1.5
4,337,760  7/1982  Rubin ........................... 424/12 X

OTHER PUBLICATIONS

Goldberg, Am. J. Ob. Gyn., vol. 107, 1970, pp. 465–471.
Jones, Brit. J. Cancer, vol. 35, 1977, pp. 885–887.
Motomiya, Urological Res., vol. 3, 1975, pp. 41–48.

Primary Examiner—Anna P. Fagelson
Attorney, Agent, or Firm—Browdy and Neimark

[57] ABSTRACT

A method of diagnosing the presence of tumors having β-glucuronidase activity comprises administering a glucuronide which differs in color or color intensity from the aglycone thereof to a patient. The preferred glucuronide is phenolphthalein glucuronide. The urine is then collecting for a twenty four hour period and the amount of phenolphthalein glucuronides present in the urine is determined. If substantially all of the phenolphthalein glucuronide is expelled then it is apparent that the body has no tumors or bacterial infections exhibiting β-glucuronidase activity. If however substantial amounts of phenolphthalein is retained, then this is an indication of the presence of tumors having β-glucuronidase activity or a bacterial infection having β-glucuronidase activity.

11 Claims, No Drawings

DIAGNOSIS OF TUMORS OR BACTERIAL INFECTIONS HAVING β-GLUCURONIDASE ACTIVITY

CROSS-REFERENCE TO RELATED APPLICATIONS

The present application is a continuation-in-part of U.S. application Ser. No. 89,888, filed Oct. 31, 1979, now U.S. Pat. No. 4,337,760, which in turn is a continuation-in-part of U.S. application Ser. No. 951,269, filed Oct. 13, 1978, U.S. application Ser. No. 951,270, filed Oct. 13, 1978, and U.S. application Ser. No. 11,619, filed Feb. 12, 1979, now U.S. Pat. No. 4,327,074 the entire contents of all of which are hereby incorporated by reference.

FIELD OF THE INVENTION

The present invention relates to a method of diagnosing tumors which are treatable by means of glucuronides having toxic aglycones and, more particularly, to a method of diagnosing tumors exhibiting β-glucuronidase activity by means of a urine test.

BACKGROUND OF THE INVENTION

The parent and grandparent applications of the present application, identified hereinabove, disclose methods and compositions for the treatment of tumors exhibiting β-glucuronidase activity or for the treatment of certain bacterial infections having β-glucuronidase activity. Since it is known that certain tumors exhibit high β-glucuronidase activity, as well as do certain bacteria, such tumors or infections may be treated by means of a glucuronide compound having an aglycone which is toxic to the tumor cell or bacterial cell. The conjugated glucuronide is non-toxic but once it comes into contact with the β-glucuronidase at the tumor site or bacteria site, the glucuronide will be deconjugated and the toxic aglycone will destroy the tumor or the bacteria directly at the site of the tumor or of the bacterial infection.

The parent and grandparent applications of the present application disclose the further improvement that the selectivity of such glucuronide compounds toward tumors can be greatly increased and the possible deconjugation of the toxic aglycones in normal parts of the body can be greatly minimized by administering to the patient, prior to or simultaneously with administration of the glucuronide, an alkalinizing agent which will maintain the pH of the rest of the body at a pH of about 7.4. It is known that at a pH of 7.4 and above, glucuronidase activity is substantially nil. Thus, the administration of alkalinizing agent, such as bicarbonates or other basic salts, will substantially decrease and eliminate β-glucuronidase activity which naturally occurs in certain healthy tissues, such as the kidneys, spleen and liver. Such an administration of alkalinizing agent will not diminish the acidity of the tumor cells themselves, however, in view of the naturally low pH of the tumor cells, the mechanism of prior hyperacidification, and the lack of substantial blood perfusion through the tumor areas, as well as other possible mechanisms.

Similarly, it has been reported that the optimum pH of bacterial β-glucuronidase is higher than the optimum pH of the β-glucuronidase of normal healthy internal organs. Therefore, upon alkalinization of the body, the β-glucuronidase activity of the organs will be substantially eliminated, while that of the bacteria, although alkalinized, will still be present.

Before treatment of patients in accordance with the processes of said parent and grandparent applications, it should be ascertained that the particular type of tumor involved has high β-glucuronidase activity. The parent and grandparent applications disclose a number of ways in which this may be done. One way is to assay tumor cells obtained in a biopsy for β-glucuronidase activity. If such a test is positive, then the pharmaceutical compositions discussed hereinabove may be administered. This method cannot be widely used as it is not always feasible to take a biopsy and a method which does not require an operation would be preferred. A second method is the administration of a glucuronide whose aglycon has been labelled with a radioactive isotope. If upon a full body scan it is found that the radioisotope is accumulated at any specific areas of the body, then this will indicate not only the location of the tumor but the fact that the tumor has sufficient β-glucuronidase activity to deconjugate the glucuronide. After this has been determined, the appropriate amount of the glucuronide of choice may be administered. If there are not tumors present, or if the tumors are of the type which do not have β-glucuronidase activity, then there will be no accumulation of radioisotope in the body as the alkalinization step of the present invention eliminates all usual β-glucuronidase activity and the isotope will be passed through the body. This also is not a preferred method as it requires the use of radioactive material and full body X-ray scans.

Another method of diagnosing tumors which are treatable by the above disclosed means is to test for the presence of free glucuronic acid in the urine. While the presence of glucuronides in the urine is common, the presence of free glucuronic acid in the urine, and particularly the presence of increasing amounts of glucuronic acid when tested over a period of several days, is a potent indication of the presence of tumors with β-glucuronidase activity. It is hypothesized that the presence of free glucuronic acid in the urine in cancer patients is caused by the action of β-glucuronidase in the cancer cells on the intercellular filaments and connective tissue. Glucuronic acid is a reaction product of such activity because the intercellular filaments and connective tissue are composed of polymers of which glucuronic acid is an element, and which are known to be substrates for the enzyme β-glucuronidase. A method for distinguishing free glucuronic acid from conjugated glucuronides in the urine is disclosed in said parent application.

This method for diagnosing tumors is a good method as it involves only a urine test. However, this test also has problems of accuracy.

SUMMARY OF THE INVENTION

Accordingly, it is an object of the present invention to overcome the deficiencies of the prior art.

It is another object of the present invention to provide a simple and accurate method for determining the presence of tumors having β-glucuronidase activity in a patient.

It is a further object of the present invention to provide a method for diagnosing the presence of tumors having β-glucuronidase activity by means of a urine test.

These and other objects of the present invention will be better understood from a reading of the following summary and the detailed description of the present invention.

The improved method of the present invention is essentially a phenolphthalein retention test. Subjects for the method of diagnosis of the present invention are administered phenolphthalein glucuronide. Healthy patients, having no tumors having $\beta$-glucuronidase activity, given a 100 mg intravenous administration of phenolphthalein glucuronide will expell more than 90% of the phenolphthalein glucuronide within 24 hours. However, if the patient has a tumor having $\beta$-glucuronidase activity, then the phenolphthalein glucuronide will become deconjugated at the tumor site by the $\beta$-glucuronidase and the phenolphthalein will stain the tumor red. It will not be expelled in the urine. Thus, if a significant amount of the phenolphthalein glucuronide is not recovered in the urine, then this is a positive indication of the presence of a tumor having $\beta$-glucuronidase activity.

DETAILED DESCRIPTION OF PREFERRED EMBODIMENT

Phenolphthalein glucuronide is a known compound which has long been used in analytical processes. See for example, Szasz, G. "Comparison Between p-Nitrophenyl Glucuronide and Phenolphthalien Glucuronide as Substrates in the Assay of $\beta$-Glucuronidase", *Clinical Chemistry*, volume 13, No. 9, pages 752-9, 1967. There are many known conventional methods for producing phenolphthalein glucuronide. One recently published method is Nambara, T. et al, "New Synthesis of Phenolphthalein Glucuronide", *Chem. Pharm. Bull.*, volume 24, No. 11, pages 2869-70, 1976.

While phenolphthalein glucuronide itself is colorless, after hydrolysis by $\beta$-glucuronidase it releases phenolphthalein which at pH values above 7 yields a characteristic violet color. It is known that 1 mg of phenolphthalein at pH 13 stains 30 liters of water.

While administering the phenolphthalein glucuronide, agents should also be administered to hyperacidify any tumor cells which may be present and to alkalinize the rest of the body. In this manner, if tumors with $\beta$-glucuronidase activity are present, the $\beta$-glucuronidase activity at the tumor site will be enhanced due to hyperacidification of the tumor cells (the optimum pH of lysosomal enzyme $\beta$-glucuronidase being about 5.2) and the $\beta$-glucuronidase activity of healthy organs will be substantially eliminated by means of alkalinization. If no tumors having $\beta$-glucuronidase activity are present, then the administration of a hyperacidifying agent, such as glucose, will have had no effect and the administration of an alkalinizing agent will still prevent deconjugation of the phenolphthalein glucuronide in healthy organs thus allowing greater recovery of the phenolphthalein glucuronide from the urine. When tumors having $\beta$-glucuronidase activity are present, this activity will hydrolyze the phenolphthalein glucuronide and the phenolphthalein will stain the cancer tissue and will not be recovered from the urine. This staining effect has a secondary advantage, of course, if administered immediately prior to surgery as the tumor tissue will then be readily apparent.

The phenolphthalein glucuronide should preferably be administrated by an intravenous drip of 100 mg phenolphthalein glucuronide in 1 liter 10% glucose and 0.1% NaHCO$_3$.

It has been found that in patients without tumors having $\beta$-glucuronidase activity, about 95% of the phenolphthalein glucuronide administered is recovered from the urine within 24 hours after administration. On the other hand, in cancer patients having tumors with $\beta$-glucuronidase activity, no more than 5% is recovered within the same 24 hour period. Thus, if a substantial portion of the administered phenolphthalein glucuronide is not recovered within 24 hours after administration, there is a strong probability that the patient has a tumor with $\beta$-glucuronidase activity, which can be treatable by means of the method of the present applications discussed hereinabove. Alternatively, a bacterial infection may be present having high $\beta$-glucuronidase activity which can also be treated in the same manner.

In order to determine the amount of phenolphthalein recovered from the urine, it must be hydrolyzed in order to obtain the characteristic violet color in an alkaline solution. Hydrolysis of the urine with $\beta$-glucuronidase is not preferred because there are natural inhibitors of $\beta$-glucuronidase in the urine. Accordingly, chemical hydrolysis is preferred which can be accomplished in any well known manner as, for example, with concentrated sulfuric acid. The preferred method is as follows:

0.2 cc of concentrated sulfuric acid is added to 0.1 cc of the urine sample in a test tube. 5 cc of a distilled water solution containing 5% of NaOH and 2.5% glycine is then added to the same test tube. The glycine is used to prevent fading.

The violet color that appears is read in a spectrophotometer and the phenolphthalein concentration is estimated according to a standard curve. The total amount of the phenolphthalein in the entire urine sample taken during the 24 hour period can then be determined by multiplying by the total amount of the urine.

While the present disclosure has referred specifically to phenolphthalein glucuronide, it should be clear to those of ordinary skill in the art that the diagnostic method of the present invention would also be operable with any glucuronide which differs in color or color intensity from the free aglycone, including a fluorescent aglycone the glucuroide of which is not fluorescent.

The hyperacidification of the tumor cells may take place either prior to or concurrent with the administration of the glucuronide. The hyperacidification of the tumor cells is caused by inducing a hyperglycemic condition in the patient. Therefore, any hyperglycemic agent may be used as the hyperacidification agent, as, for example, glucose in the form of honey, glucose, or other glucose containing sugar, fructose, galactose, lactose or glucagon. Furthermore, it should be understood that this hyperglycemic condition may be effected in any known manner. For example, if the patient is diabetic, then the condition can be brought about by decreasing insulin administration.

Any agent which will raise the pH of the urine to approximately 7.4 can be used as the alkalinizing agent, including sodium or potassium bicarbonate or citrate, or other basic salts or antacids. While it is preferred that these be administered intravenously, they may be administered orally. The alkalinizing agent should be administered in an amount sufficient to raise the pH of the urine to approximately 7.4, as this will indicate that the pH level of the body has been raised to about that level. pH levels slightly above or below 7.4 may of course also be used, although not preferred.

Besides intravenous administration, the phenolphthalein glucuronides may be administered by any means of parenteral adminstration. However, it should not be administered orally as it is known that β-glucuronidase is present in the digestive tract.

It will be obvious to those skilled in the art that various changes may be made without departing from the scope of the invention and the invention is not to be considered limited to what is described in the specification.

What is claimed is:

1. A method for diagnosing the presence of tumors or bacterial infections having β-glucuronidase activity, in a patient, comprising:

injecting a non-toxic conjugated glucuronide of an aglycone, which aglycone, in the free state thereof, differs in color, color intensity, or fluorescence from the conjugated glucuronide thereof;

collecting the urine of the patient for a period of time sufficient to permit most of the injected glcuronide to be expelled from the body if it is not retained therein; and determining the amount of glucuronide present in the collected urine by deconjugating the glucuronide in a sample of the urine and comparing the color, color intensity or fluorescence of the aglycone with a standard curve, thus indicating the quantity of aglycone in the sample;

whereby, if it appears that a substantial amount of glucuronide has been retained in the body, this is a positive indication of a tumor or bacterial infection having β-glucuronidase activity.

2. A method in accordance with claim 1, wherein said glucuronide is phenolphthalein glucuronide.

3. A method in accordance with claims 1 or 2, wherein the urine is collected for a period of twenty four hours.

4. A method in accordance with claim 2, wherein the urine is analyzed by taking a sample of the urine, deconjugating the phenolphthalein glucuronide, alkalinizing and comparing the color intensity with a standard curve, thus indicating the quantity of phenolphthalein in the sample.

5. A method in accordance with claim 4, wherein said glucuronide is deconjugated by treating with a concentrated mineral acid.

6. A method in accordance with claim 1, wherein prior to or concurrent with administration of the glucuronide a hyperacidifying agent is added to hyperacidify any tumor cells which may be present.

7. A process in accordance with claim 1 or claim 6, wherein previous to or concurrent with administration of the glucuronide an alkalinizing agent is added in an amount sufficient to maintain the pH level of the non-tumor tissues of the patient at approximately 7.4 during the glucuronide treatment.

8. A process in accordance with claim 6, wherein said hyperacidifying agent comprises a hyperglycemic agent.

9. A process in accordance with claim 7, wherein said hyperacidifying agent comprises a hyperglycemic agent.

10. A process in accordance with claim 8 or claim 9, wherein the hyperglycemic agent is selected from the group consisting of glucose, fructose, galactose, lactose and glucogan.

11. A process in accordance with claim 7, wherein said alkalinizing agent comprises an alkali metal bicarbonate or citrate.

* * * * *